United States Patent [19]

Wilk

[11] Patent Number: 5,279,599
[45] Date of Patent: Jan. 18, 1994

[54] EVACUATOR ASSEMBLY'S METHOD OF USE HAVING SELECTIVELY REMOVABLE COVERS

[76] Inventor: Peter J. Wilk, 185 W. End Ave., New York, N.Y. 10023

[21] Appl. No.: 839,301

[22] Filed: Feb. 20, 1992

Related U.S. Application Data

[63] Continuation-in-part of Ser. No. 530,214, May 30, 1990.

[51] Int. Cl.$^5$ .............................................. A61M 1/00
[52] U.S. Cl. ................................. 604/317; 604/280; 604/313
[58] Field of Search ............. 604/35, 31, 73, 264, 604/280, 281, 313, 315, 316, 317, 319, 902; 128/760, 761, 767, 206.28; 239/562

[56] References Cited

U.S. PATENT DOCUMENTS

| | | | |
|---|---|---|---|
| 2,972,346 | 2/1961 | Eddings | 604/313 |
| 3,237,872 | 3/1966 | Mincy | 239/562 |
| 3,403,677 | 10/1965 | Struve . | |
| 3,625,207 | 12/1971 | Agnew | 128/206.28 |
| 4,419,301 | 12/1983 | Nahra et al. . | |
| 4,452,397 | 6/1984 | Barton | 239/562 |
| 4,778,111 | 10/1988 | Leap | 239/562 |
| 4,921,492 | 5/1990 | Schultz et al. . | |
| 4,925,452 | 5/1990 | Melinyshyn et al. . | |
| 5,015,243 | 5/1991 | Schifano | 604/315 |
| 5,127,411 | 7/1993 | Schoolman et al. . | |
| 5,215,539 | 6/1993 | Schoolman . | |

OTHER PUBLICATIONS

Laser Technologies Group 1989 Plume-Away Promotional Brochure.

Primary Examiner—Randall L. Green
Assistant Examiner—Rob Clarke
Attorney, Agent, or Firm—R. Neil Sudol; Henry D. Coleman

[57] ABSTRACT

A device connectable to a suction source for drawing off particulate matter from the air about a burning site comprises a flexible hose provided along an end segment with a plurality of spaced apertures, the apertures being covered by punch-outs in the wall of the tube. A fastener serves to connect the hose at an end opposite the apertured end segment to the suction source, and a coupling element is provided for securing a free tip of the hose, at the free end of the apertured end segment, to the hose along a middle portion thereof to thereby form a loop including at least a portion of the apertured end segment. A selectable number of the punch-outs may be removed from the hose prior to a burning operation.

12 Claims, 3 Drawing Sheets

5,279,599

EVACUATOR ASSEMBLY'S METHOD OF USE HAVING SELECTIVELY REMOVABLE COVERS

CROSS-REFERENCE TO RELATED APPLICATION

This application is a continuation-in-part of commonly owned U.S. patent application Ser. No. 530,214 filed May 30, 1990.

BACKGROUND OF THE INVENTION

This invention relates to an assembly or device for drawing off gases and particulate matter from a burning site. In surgical applications, such an assembly is useful as a plume evacuator for removing the gases and particulate matter generated at a surgical site where a laser is being used. This invention also relates to an associated surgical method for use in drawing off gases and particulate matter from a cauterization site.

Lasers are employed in dermatological surgery to remove such skin conditions as warts and cancerous tissues. A laser burns off the unwanted tissues and in so doing generates an odiferous by-product known as a "plume." The plume includes gases and particular matter and may further include bacteria and viruses such as the AIDS virus. Accordingly, it is important to evacuate the plume from the surgical environs as effectively as possible.

A plume evacuator currently on the market comprises a rigid hollow ring provided on an inwardly facing surface with a series of holes. The ring is connected to a vacuum generator and placed around the surgical site. During the laser operation, the vacuum generator or pump draws off the plume through the holes in the ring. The vacuum unit includes a filter which filters out the particulate matter. The filtered air is then returned to the operating room.

A disadvantage with that plume evacuator is that the fixed nature of the ring is not adaptable to the particular surgical conditions. For example, the ring is of a fixed diameter and cannot be adapted to differently sized surgical sites. This reduces the efficiency of the evacuator and may in some circumstances allow a portion of the plume to escape into the ambient atmosphere.

OBJECTS OF THE INVENTION

An object of the present invention is to provide an improved plume evacuator.

Another object of the present invention is to provide a plume evacuator which is easily adaptable to different surgical conditions.

A more particular object of the present invention is to provide such a plume evacuator which can be adjusted to surround surgical sites of different sizes.

A further specific object of the present invention is to provide such a plume evacuator which is at least partially conformable to a surface about a surgical site.

Yet a further specific object of the present invention is to provide a plume evacuator which is adaptable to the shape of a surgical site.

An additional object of the present invention is to provide a plume evacuator which can be located at a varying distance from a surgical site.

Another object of the present invention is to provide a method for use in cauterization surgery to draw off gases and air-borne particulate matter from a surgical site.

Yet another object of the present invention is to provide such a method which facilitates the adaptation of plume evacuation to particular surgical conditions.

These and other objects of the present invention will be apparent from the drawings and detailed descriptions herein.

SUMMARY OF THE INVENTION

A device connectable to a suction source for drawing off particulate matter from the air about a burning site comprises, in accordance with a general embodiment of the present invention, an at least partially hollow body which is extended so as to at least partially surround the burning site. The hollow body is provided with a plurality of closed apertures. A plurality of selectably removable covers are provided on the hollow body at the apertures for keeping the apertures closed and for enabling the opening of selected ones of the apertures immediately prior to a burning operation. A fastening element is provided for detachably connecting the hollow body to the suction source.

The covers or removable closure elements on the hollow body preferably take the form of punch-outs in a wall of the hollow body. The punch-out form of the covers or closure elements facilitates an inexpensive mass production of the smoke evacuator device.

A specific embodiment of a device connectable to a suction source for drawing off and particulate matter from the air about a burning site comprises, in accordance with the present invention, a flexible hose provided along an end segment with a plurality of spaced apertures and covers attached to the hose for removably covering at least some of the apertures. A fastening element is provided for detachably connecting the hose at an end opposite the segment to the suction source.

As mentioned hereinabove, the covers over the apertures in the hose preferably take the form of punch-outs in the wall of the hose. Prior to a burning operation, for example, laser surgery, a selectable number of punch-outs are removed to open selected apertures, thereby optimizing the draw of the suction tube at the burning site.

Pursuant to another feature of the present invention, a form retention component is attached to the hose for maintaining at least a portion of the hose in a selected substantially loopshaped configuration. The form retention component may take the form of a tie string, an endless loop, a clip, hook, or other coupling element at the distal end of the hose (opposite the fastening element) for securing a free tip of the hose to a middle portion thereof to thereby form a loop. The form retention component may alternatively take the form of an adhesive strip or other means for releasably attaching the hose to a surface around the burning site. As yet another alternative, the form retention component may include a bendable metal strip attached to the hose (for example, inside the hose) for maintaining the hose in an at least partially arcuate configuration formed by manipulation of the hose.

Pursuant to another feature of the present invention, the smoke evacuator further comprises means attachable to the hose for varying the distance of the loop from the burning site.

The present invention provides an improved plume evacuator which is easily adaptable to different surgical conditions. The evacuator can be adjusted to surround surgical sites of different sizes insofar as the size of the loop which surrounds the surgical site is selected by the surgeon or assistant prior to the operation. Moreover, a plume evacuator in accordance with the present invention is at least partially conformable to a surface about a surgical site. The bendable metal strip and the releasable attachment component (e.g., adhesive strip), either individually or in combination with one another, allow the hose to assume the contour of the patient's body in a region about the surgical site.

The selectably openable apertures in a plume evacuator in accordance with the present invention enable a surgeon or surgical assistant to optimize the locations of suction along the hose. Only the apertures which are most closely juxtaposed to the surgical site are opened and allowed to draw smoke. Apertures in the hose which are too far from the surgical site, after the hose has been properly configured and disposed about the surgical site, remain closed, thereby maximizing suction through the apertures closest to the source of the plume.

Furthermore, a plume evacuator in accordance with the present invention can be located at a varying distance from a surgical site. More specifically, the hose may be attached to a foam strip which is provided with an adhesive surface for attachment to the patient's body in a region about the surgical site. The foam strip or other pad distances the evacuator hose from the skin surface and thereby enables an optimizing of the location of the suction apertures relative to the surgical site.

In accordance with the present invention, a method for use in surgery to reduce air borne particles carrying infectious micro-organisms comprises the step of providing an at least partially hollow body provided with extension means for at least partially surrounding a surgical site on a patient and further provided with a plurality of closed apertures and a plurality of selectively removable covers attached to the hollow body to cover the apertures. The method further comprises the steps of detachably connecting the hollow body to a suction source, disposing the extension means on a skin surface of a patient so that at least a portion of the hollow body is juxtaposed to the surgical site on the patient, and displacing selected ones of the covers from the hollow body so as to open corresponding ones of the apertures juxtaposed to the surgical site. Organic tissues are subsequently cauterized from the surgical site, thereby generating air-borne particulate matter. During the cauterization procedure, the suction source is operated to apply suction to the hollow body and thereby draw off particulate matter from the air about the surgical site.

The hollow body is preferably a bendable hose, the method further comprising the step of forming the hose into an at least partially arcuate configuration, which is juxtaposed to the surgical site during disposition of the hose on the skin of the patient.

DETAILED DESCRIPTION

Figure 1:
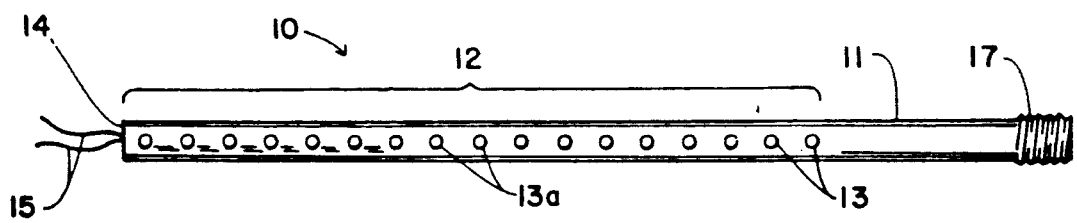
FIG. 1 is an elevational side view of a plume evacuator hose in accordance with the present invention.

As illustrated in FIG. 1, a plume evacuator device 10 comprises a flexible hose 11 provided along an end segment 12 with a plurality of equispaced equal-sized apertures 13 each stopped by a respective punch-out cover 13a formed from the sidewall of hose 11. At a free tip 14 of end segment 12, hose 11 is provided with a pair of tie strings 15 for detachably securing the hose tip to a middle portion of the hose to form a loop 16, illustrated in FIG. 4. At an end opposite tie strings 15 and perforated end segment 12, hose 11 is provided with a fastener part 17 for connecting the hose to a suction source or vacuum generator 18 (FIG. 4).

Figure 2:
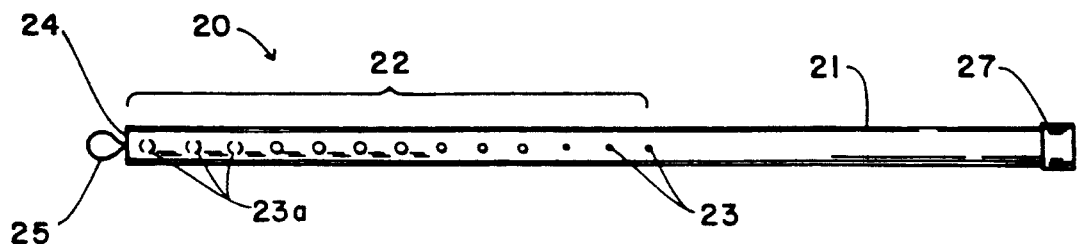
FIG. 2 is an elevational side view of another plume evacuator hose in accordance with the present invention.

Another plume evacuator device 20 is illustrated in FIG. 2. Device 20 similarly takes the form of a flexible hose 21, preferably made of synthetic resin material such as polyethylene, polypropylene, nylon or polytetrafluoroethylene. Hose 21 is provided along an end segment 22 with a linear array of substantially equispaced circular apertures 23 having diameters which decrease in a monotonic sequence from a free hose tip 24 towards an end of hose 21 which is provided with a coupling member 27 for connecting that hose end to suction source or vacuum generator 18 (FIG. 4). Apertures 23 are covered by respective punch-outs 23a formed in the sidewall of hose 21. At free tip or end 24, hose 21 is provided with a small loop 25 preferably made of an elastic synthetic resin material.

Figure 3:
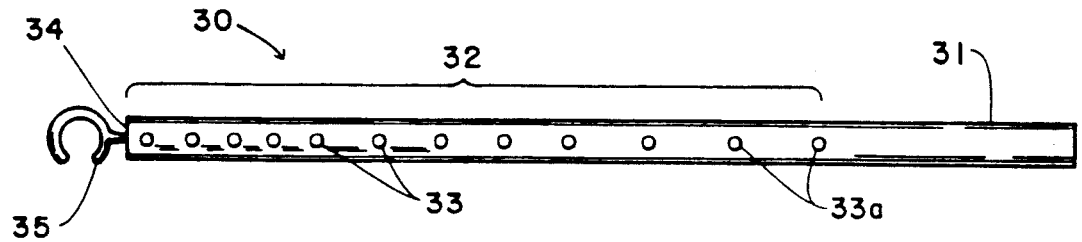
FIG. 3 is an elevational side view of yet another plume evacuator hose in accordance with the present invention.

Yet another plume evacuator assembly 30 is depicted in FIG. 3. Again, that plume evactuator assembly comprises a flexible synthetic resin hose 31 provided along an end segment 32 with a linear array of circular apertures 33 stopped by respective punch-out covers 33a formed from the sidewall of hose 31. Apertures 33 or punch-out perforations 33a have essentially the same diameter but are spaced at distances from each other which increase in a monotonic manner from a free hose tip 34 towards an end 37 of hose 31 which is connectable to suction source of vacuum generator 18 (FIG. 4). Hose end 37 is sufficiently resilient, for example, to receive a male inlet member (not illustrated) of suction source or vacuum generator 18 in an airtight friction fit. At free tip or end 34, hose 31 is provided with a resilient clip fastener or coupling element 35 for securing hose tip 34 to hose 31 along a middle portion thereof to form a loop, as shown in FIG. 4.

Figure 4:
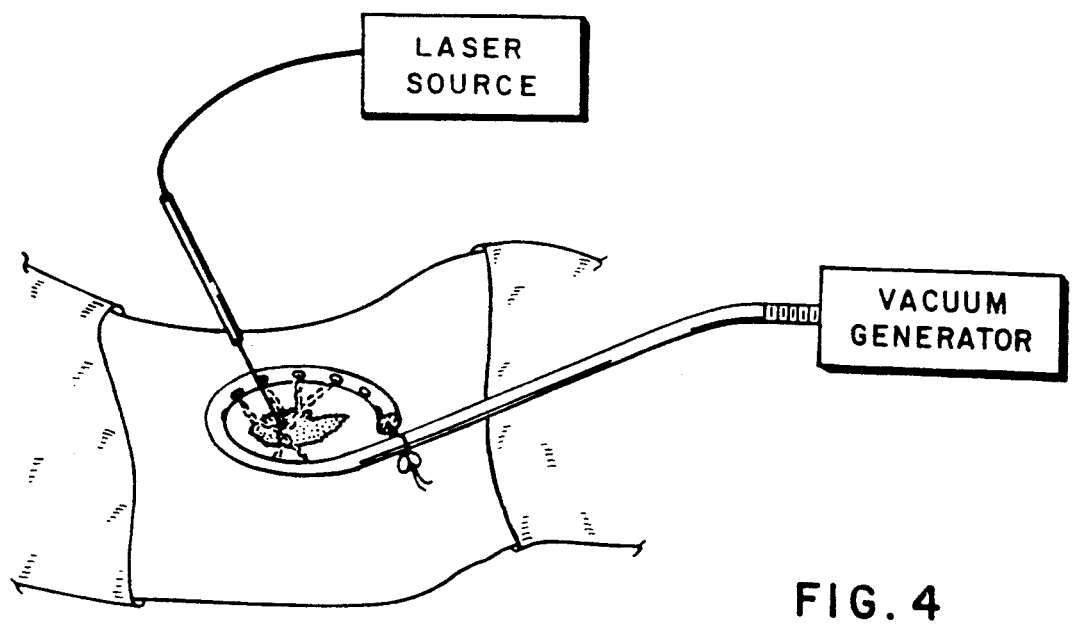
FIG. 4 is a diagrammatic perspective view of the plume evacuator hose of FIG. 1, showing the evacuator hose connected to a vacuum generator and in use during a surgical operation.

In use of a plume evacuator device 10, 20, or 30, as depicted in FIG. 4 with reference particularly to device 10, the fastener part or coupling member 17, 27 or 37 is connected to suction source of vacuum generator 18. With respect to plume evacuator device 20, hose 21 is first brought through loop 25 and then end 37 is connected to the vacuum generator.

Upon the connection of hose 10 or 30 to vacuum generator 18, the end segment 12 or 32 is then turned back upon itself to form loop 16 of a desired size. Upon the formation of loop 16, which is adapted to the size and location of a surgical site 40 on a patient's body 41, strings 15 or clip fastener 35 are fastened about a middle portion of the respective hose 11 or 31 to maintain the end 14 or 34 in the shape of loop 16.

With respect to plume evacuator device 20, the loop (see loop 16 in FIG. 4) is formed prior to the connection of hose 21 to vacuum generator 18. The size of the loop may be adjusted to the specific surgical conditions either before or after connection of hose 21 to vacuum generator 18.

During a cauterization or burning operation performed by a surgeon using a laser instrument 43 connected to a laser source 44, smoke 45 resulting from the burning of the skin tissues by a laser beam 46 is sucked through apertures 13, 23 or 33 which are opened prior to the commencement of the laser operation by pushing out the respective punch-out covers 13a, 23a, 33a. The smoke is then sucked along the length of the respective hose 11, 21 or 31 to vacuum generator 18 where the air is filtered of particulate material and possible gaseous substances and returned to the air of the operating room or, alternatively, to a disposal conduit.

Figure 5:
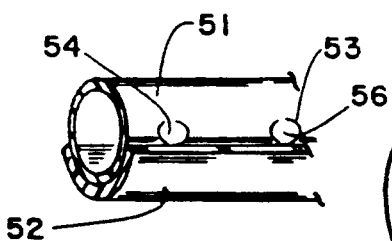
FIG. 5 is a partial cross-sectional side view of another embodiment of an evacuator hose in accordance with the present invention.

As illustrated in FIG. 5, a plume evacuator hose 51, which may take the form of hose 11, 21, or 31, is provided along a longitudinally extending surface with an adhesive strip 52 for releasably attaching the evacuator hose to a patient's skin about a surgical site. Adhesive strip 52 serves to fix the hose at the surgical site so that it does not shift during the surgical procedure. In addition, the adhesive strip serves to conform hose 51 to the shapes of the patient's body in a region about the surgical site.

In its sidewall, hose 51 is provided with a plurality of circular score lines 53 which define a plurality of spaced apertures 54 which closed by respective covers 56 integral with the hose sidewall. Selected covers 56 may be pressed inwardly into hose 51, thereby shearing those covers from hose 51 and opening the respective apertures 54. This punching out of the aperture covers 56, as well as aperture covers of any other hose embodiment disclosed herein, is undertaken after the respective hose, e.g., hose 51, has been configured to conform to a surgical site. The removal of selected covers 13a, 23a, 33a, 56, etc., to open the apertures 13, 23, 33, 54, etc., closest to the surgical site may be undertaken while the respective hose, 11, 21, 31, 51 is located on the patient. Alternatively, the hose may be temporarily removed from the patient, the holes punched and the hose replaced in the original position and configuration.

Figure 6:
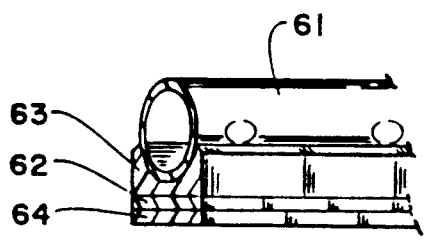
FIG. 6 is a partial cross-sectional side view of an additional embodiment of an evacuator hose in accordance with the present invention.

As depicted in FIG. 6, a plume evacuator hose 61, which may take the form of hose 11, 21, or 31, is provided along a longitudinally extending surface with an adhesive strip 62 attached to the hose via a buffer strip or cushion 63. Cushion 63 is made of a resilient foam-like material and serves to maximize the surface of the adhesive strip 62 which is in contact with the patient's skin surface at the surgical site. Adhesive strip 62 is preferably a two-sided adhesive strip and is covered, during shipping and prior to use of the plume evacuator, with a release liner 64.

Figure 7:
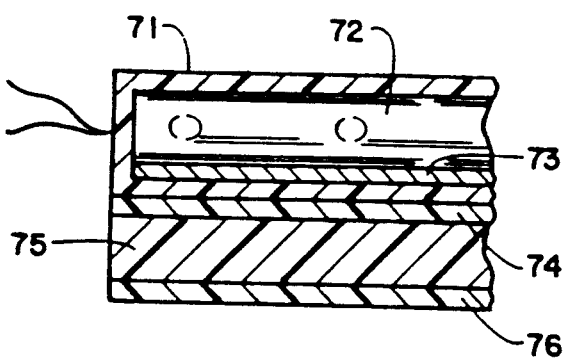
FIG. 7 is a partial cross-sectional side view of a further embodiment of an evacuator hose in accordance with the present invention.

As illustrated in FIG. 7, another plume evacuator hose 71 in accordance with the present invention is provided on an inner surface 72 with memory strip 73 in the form of an elongate metallic member. A two-sided adhesive strip 74 joins to an outer surface of hose 71 an elongate spacer member 75 which serves to set hose 71 at a distance from a surgical site, in a direction measured generally perpendicularly to the surface of the site. Spacer member 75 is provided along a side opposite tube or hose 71 with an adhesive layer 76 for attaching the hose to the patient's skin about the site of the surgery.

Figure 8:
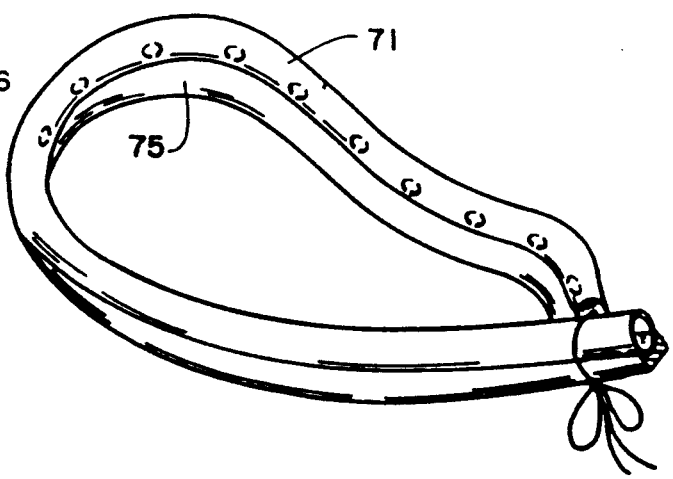
FIG. 8 is a partial perspective view of the evacuator hose of FIG. 7 in a use configuration.

As shown in FIG. 8, memory strip 73 enables a surgeon or surgical assistant to form hose 71 into a variety of shapes each corresponding to the shape of a particular surgical site.

It is to be noted that memory strip 73 may be embedded in the wall of hose 71 or may, alternatively, be fastened to the outside of the hose.

Figure 9:
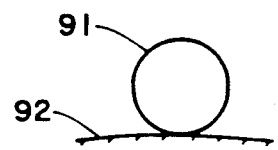
FIG. 9 is a diagrammatic end view of a plume evacuator hose in accordance with the present invention, showing that hose in relation to a skin surface.
Figure 10:
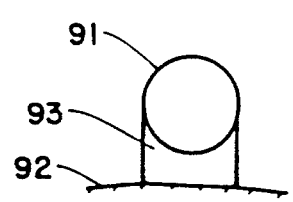
FIG. 10 is a diagrammatic end view of the plume evacuator hose of FIG. 9, showing that hose in another relation to the skin surface.
Figure 11:
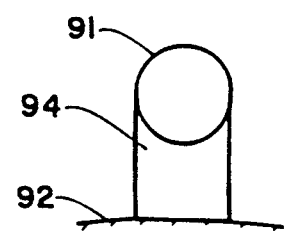
FIG. 11 is a diagrammatic end view of the plume evacuator hose of FIG. 9, showing that hose in yet another relation to the skin surface.

FIGS. 9, 10 and 11 diagrammatically illustrate three different relationships between a hose 91 and a skin surface 92. In FIG. 9, the hose is in direct contact with the skin surface. In FIG. 10, hose 91 is elevated above skin surface 92 by virtue of a spacer member 93. In FIG. 11, hose 91 is spaced a greater distance from skin surface 92 by interposition of a wider spacer member 94. Each tube or hose 91 may be sold with a plurality of spacer members 93 and 94, the surgeon or surgical assistant selecting the appropriate spacer member for the particular surgery to be performed. Generally, the larger the area at which the burning procedure is to be implemented, the wider the spacer member and the farther the hose 91 from the surgical site in the orthogonal direction.

It is to be noted that an evacuator hose in accordance with the invention is able to retain a selected loop-shaped form by the operation of tie strings 15, loop 25, or clip fastener 35, and/or by the operation of adhesive strip or layer 52, 62 or 76, and/or by the operation of metal memory strip 73.

Figure 12:
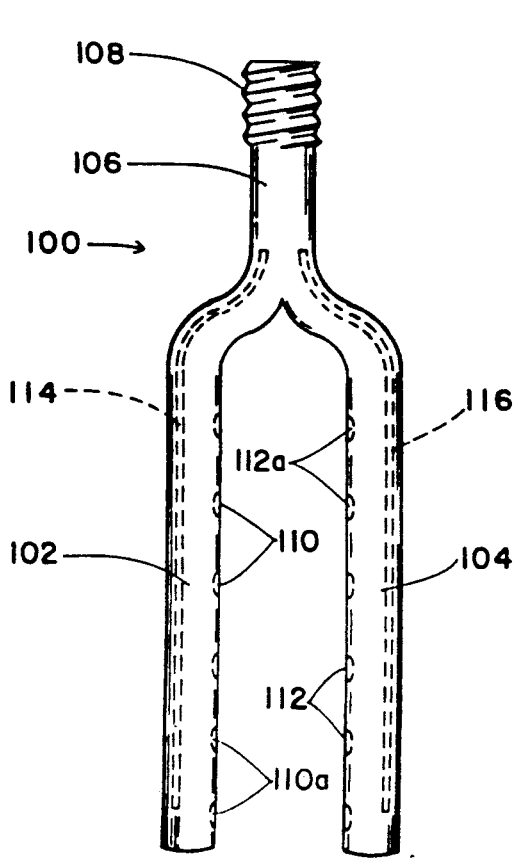
FIG. 12 is a top view of another plume evacuator hose in accordance with the present invention.

As illustrated in FIG. 12, a plume evacuator hose 100 has a pair of flexible hollow prong sections 102 and 104 joined to one another at one end of a connector section 106 of hose 100. Connector section 106 is provided at an end opposite prong sections 102 and 104 with a coupling feature 108.

Prong sections 102 and 104 are provided along facing surfaces with a plurality of longitudinally spaced apertures 110 and 112 which are covered by respective punch-outs 110a and 112a formed in the sidewalls of prong sections 102 and 104. Each prong section 102 and 104 is further provided with a respective bendable metal strip or rod 114 and 116 attached along a internal surface of the prong section, possibly by embedding the strip or rod in the flexible polymeric material of hose 100.

Figure 13:
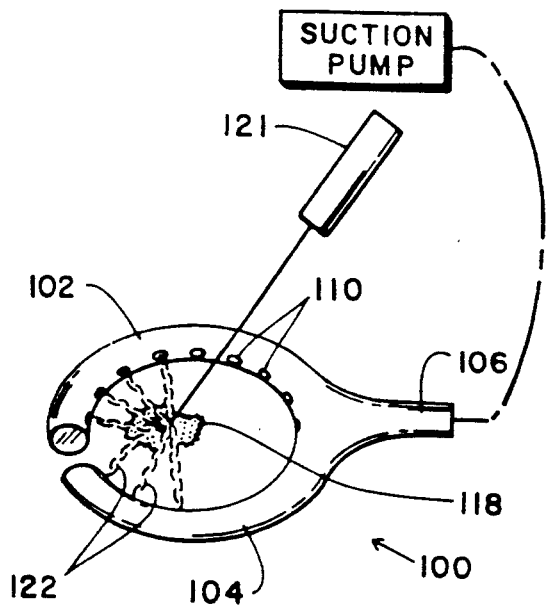
FIG. 13 is a diagrammatic perspective view of the plume evacuator hose of FIG. 12, showing the evacuator hose connected to a vacuum generator and in use during a surgical operation.

As shown in FIG. 13, prong sections 102 and 104 of hose 100 can be deformed, by virtue of bendable metal strips 114 and 116, to assume a circular or loop-shaped form disposable about a surgical site 118 on a patient's skin surface. Upon connection of hose 100 to a suction pump 120 via coupling 108, an activation of suction pump 120, and a burning or cauterization of diseased skin tissue at the surgical site by a laser device 121, particle laden air 122 is sucked through opened apertures 110 and 112 into prong sections 102 and 104.

Figure 14:
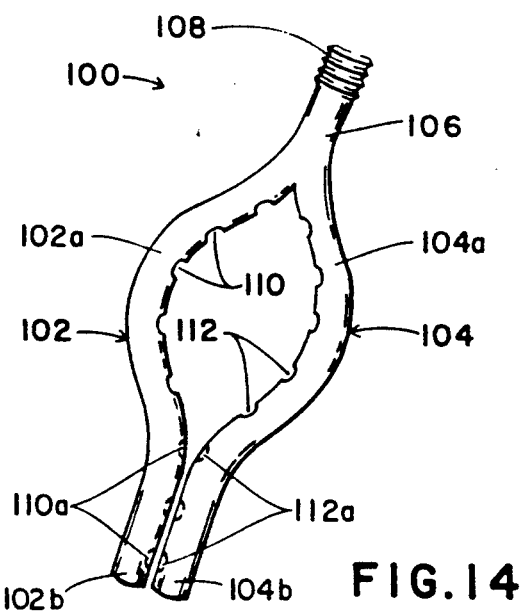
FIG. 14 is a top view of the plume evacuator hose of FIG. 12 in another use configuration.

As depicted in FIG. 14, prong sections 102 and 104 may be bent in other ways to provide other loop-shaped forms of differing sizes and shapes, to adapt hose 100 to the particular surgical conditions. As further depicted in FIG. 14, apertures 110 and 112 disposed along arcuate portions 102a and 104a of prongs 102 and 104 which have been bent to surround a surgical site (e.g., 118 in FIG. 13) have been opened, while other apertures along end portions 102b and 104b which are not juxtaposed to the surgical site remain closed by their respective punch-out covers 110a and 112a. In contrast, in the use configuration shown in FIG. 13, it is possible that all of the apertures 110 and 112 of prongs 102 and 104 are sufficiently close to the surgical site 118 to justify removal of all the covers 110a and It is to be noted that the punch-outs or covers 13a, 23a, 33a, 110a, 112a which close the plume evacuator suction apertures 13, 23, 33, 110, 112 may be removed via the aid of any convenient surgical tool, such as a clamp or forceps. Even a pen may be used.

Figure 15:
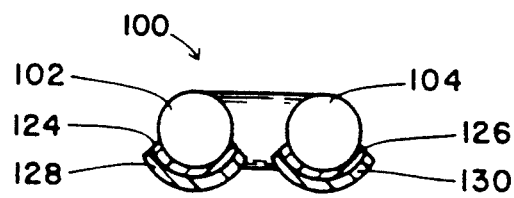
FIG. 15 is a diagrammatic end view of the plume evacuator hose of FIG. 12.
Figure 16:
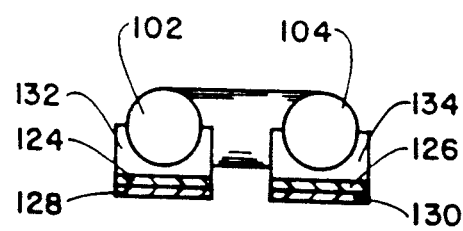
FIG. 16 is a diagrammatic end view of another plume evacuator hose similar to the hose of FIG. 12.

As shown in FIG. 15, prong sections 102 and 104 are provided along lower surfaces with respective two-sided adhesive strips 124 and 126 each covered prior to use of hose 100 by respective release liners 128 and 130. FIG. 16 illustrates that resilient spacer strips 132 and 134 may be provided between adhesive strips 124 and 126, on the one hand, and prong sections 102 and 104, one the other hand, to increase the contact area between the adhesive strips and a skin surface to which prong sections 102 and 104 are to be attached during a surgical procedure.

Figure 17:
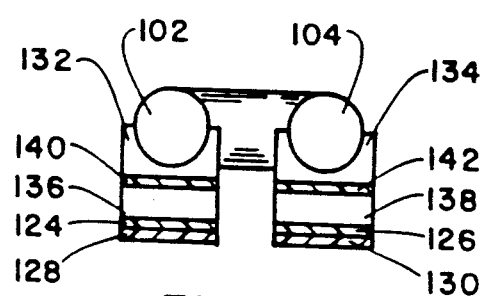
FIG. 17 is a diagrammatic end view of yet another plume evacuator hose similar to the hoses of FIGS. 12 and 16.

As depicted in FIG. 17, further spacer elements 136 and 138 together with respective adhesive layers 140 and 142 may be inserted between two-sided adhesive strips 124 and 126, on the one hand, and spacer strips 132 and 134, on the other hand, to further increase the distance between prong sections 102 and 104 and the patient's skin surface to optimize suction during a surgical procedure.

Although the invention has been described in terms of particular embodiments and applications, one of ordinary skill in the art, in light of this teaching, can generate additional embodiments and modifications without departing from the spirit of or exceeding the scope of the claimed invention. For example, other methods of covering or closing apertures 13, 23, 33, 54, 110, 112, . . . are possible so that they may be easily and selectively opened prior to a surgical operation. One such method involves the placement of a plurality of adhesive strips over respective hose apertures. To open the apertures selected because of their proximity to the surgical site, the respective adhesive strips are peeled away from the hose. Alternatively, a single adhesive strip may cover all of the suction apertures along the hose. Opening the selected apertures is accomplished by perforating the tape through selected apertures by using an appropriate instrument.

Accordingly, it is to be understood that the drawings and descriptions herein are preferred by way of example to facilitate comprehension of the invention and should not be construed to limit the scope thereof.

What is claimed is:

1. A method for use in surgery to reduce air borne particles carrying infectious micro-organisms, comprising the steps of:
   providing a substantially flexible hose with a plurality of apertures spaced along at least one end segment and a plurality of three or more selectively removable covers attached to said hose to cover said apertures;
   detachably connecting said hose at an end opposite said segment to a suction source;
   forming at least a portion said hose into an arcuate configuration;
   disposing said portion of said hose on a skin surface of a patient so that said arcuate configuration is juxtaposed to a surgical site on the patient;
   displacing selected ones of said covers from said hose so as to open corresponding ones of said apertures juxtaposed to said surgical site;
   exerting a force on said portion of said hose to maintain said portion of said hose in said arcuate configuration during a surgical procedure;
   cauterizing organic tissues from said surgical site;
   generating air-borne particulate matter as a by-product of said step of cauterizing; and
   during said step of cauterizing, operating said suction source to apply suction to said hose and thereby draw off particulate matter from the air about said surgical site.

2. The method defined in claim 1, further comprising the step of releasably attaching said portion of said hose to said skin surface.

3. The method defined in claim 2 wherein said step of releasably attaching includes the step of applying an adhesive strip to said skin surface, said adhesive strip being attached to said portion of said hose.

4. The method defined in claim 3 wherein said portion of said hose is maintained in said arcuate configuration at least in part via said adhesive strip.

5. The method defined in claim 1 wherein said portion of said hose is provided with bendable means attached to said hose for maintaining said hose in a predetermined configuration formed by manipulation of said hose, said force being exerted on said portion of said hose at least in part by said bendable means.

6. The method defined in claim 1, further comprising the step of fastening a free end of said hose to a middle portion of said hose, said portion of said hose being maintained in said arcuate configuration at least in part by virtue of said step of fastening.

7. The method defined in claim 6 wherein said step of fastening includes the step of clipping said free end of said hose to said middle portion of said hose.

8. The method defined in claim 6 wherein said step of fastening includes the step of tying said free end of said hose to said middle portion of said hose.

9. The method defined in claim 1, further comprising the steps of providing said hose with a spacer element and attaching said spacer element to said skin surface to control the distance of said arcuate configuration from said surgical site.

10. The method defined in claim 1 wherein said hose is bifurcated along said hose into two hose sections each provided with a plurality of spaced apertures, said step of forming including the step of bending at least a portion of one of said hose sections into an arcuate shape.

11. The method for use in surgery to reduce air borne particles carrying infectious micro-organisms, comprising the steps of:

providing an at least partially hollow body provided with extension means for at least partially surrounding a surgical site on a patient and further provided with a plurality of closed apertures and a plurality of three of more selectively removable covers attached to said hollow body to cover said apertures;

detachably connecting said hollow body to a suction source;

disposing said extension means on a skin surface of a patient so that at least a portion of said hollow body is juxtaposed to the surgical site on the patient;

displacing selected ones of said covers from said hollow body so as to open corresponding ones of said apertures juxtaposed to said surgical site;

cauterizing organic tissues from said surgical site;

generating air-borne particulate matter as a by-product of said step of cauterizing; and during said step of cauterizing, operating said suction source to apply suction to said hollow body and thereby draw off particulate matter from the air about said surgical site.

12. The method defined in claim 11 wherein said hollow body is a bendable hose, further comprising the step of forming said hose into an at least partially arcuate configuration, said arcuate configuration being juxtaposed to said surgical site during said step of disposing.

* * * * *

UNITED STATES PATENT AND TRADEMARK OFFICE
CERTIFICATE OF CORRECTION

PATENT NO. : 5,279,599
DATED : Jan. 18, 1994
INVENTOR(S) : Peter J. Wilk

It is certified that error appears in the above-indentified patent and that said Letters Patent is hereby corrected as shown below:

Column 1, line 25, change "particular" to --particulate--; line 28, change "late" to --ate--.

Column 2, line 28, delete "and".

Column 5, line 60, insert --are-- after "which".

Column 7, line 2, change "a" to --an--; line 30, insert --112a.-- after "and"; line 43, change "one" to --on--.

Column 8, line 20 (claim 1), insert --of-- after "portion".

Column 9, line 8 (claim 11), change "The" to --A--; line 15 (claim 11), change "of" (second occurrence) to --or--.

Signed and Sealed this

Twenty-seventh Day of December, 1994

Attest:

BRUCE LEHMAN

*Attesting Officer*     *Commissioner of Patents and Trademarks*